United States Patent
Grundei et al.

[19]

[11] Patent Number: 6,120,544
[45] Date of Patent: Sep. 19, 2000

[54] FEMUR ENDOPROSTHESIS FOR ARTICIAL HIP JOINT

[75] Inventors: Hans Grundei, Lübeck, Germany; Wolfram Thomas, Rome, Italy

[73] Assignee: ESKA Implants GmbH & Co., Lübeck, Germany

[21] Appl. No.: 09/079,618

[22] Filed: May 15, 1998

[30] Foreign Application Priority Data

May 16, 1997 [DE] Germany .......................... 197 20 493

[51] Int. Cl.⁷ .............................. A61F 2/32; A61F 2/28; A61F 2/36
[52] U.S. Cl. .................................. 623/22; 16/23
[58] Field of Search ................... 623/23, 16, 22

[56] References Cited

U.S. PATENT DOCUMENTS

| | | | |
|---|---|---|---|
| 3,064,645 | 1/1962 | Ficat et al. | 623/23 |
| 3,848,273 | 11/1974 | Frey | 623/23 |
| 4,608,055 | 8/1986 | Morrey et al. | 623/23 |
| 5,015,256 | 5/1991 | Bruce et al. | 623/18 |
| 5,178,201 | 1/1993 | Ahlers | 164/34 |
| 5,433,750 | 7/1995 | Gradinger et al. | 623/16 |
| 5,897,592 | 4/1999 | Caldarise et al. | 623/16 |

FOREIGN PATENT DOCUMENTS

| | | |
|---|---|---|
| 0485311 A1 | 11/1991 | European Pat. Off. . |
| 485 311 A1 | 11/1991 | European Pat. Off. . |
| 579 868 A2 | 1/1998 | European Pat. Off. . |
| 2-213342 | 8/1990 | Japan . |
| 4-503181 | 11/1990 | Japan . |
| 5-509006 | 6/1991 | Japan . |
| WO 81/01510 | 6/1981 | WIPO . |
| WO 89/11837 | 12/1989 | WIPO . |
| WO 91/07932 | 6/1991 | WIPO . |
| WO 91/18559 | 12/1991 | WIPO . |
| 93/16663 | 9/1993 | WIPO . |

Primary Examiner—Michael J. Milano
Assistant Examiner—Hieu Phan
Attorney, Agent, or Firm—Akin, Gump, Strauss, Hauer & Feld, L.L.P.

[57] ABSTRACT

A femur endoprosthesis for an artificial hip joint is provided with a stem (1) which can be implanted without cement in the upper region of a femur below the greater trochanter. The proximal end (8) of the stem is connectable with an adapter (2) for accommodating an artificial spherical part of a joint (20). The exterior of the stem is at least partially covered with an open-meshed three-dimensional spatial lattice structure (9). A distal end of the stem is bent caudally with a caudally oriented step (31) in the transition area and constructed as a stem end (30), which is also at least partially covered with an open-meshed three-dimensional spatial lattice structure (9).

12 Claims, 1 Drawing Sheet

FEMUR ENDOPROSTHESIS FOR ARTICIAL HIP JOINT

BACKGROUND OF THE INVENTION

The present invention is directed to a femur endoprosthesis for an artificial hip joint, which is an alternative to the femur endoprosthesis in accordance with German patent 196 01 340 (U.S. patent application Ser. No. 08/783,476, the disclosure of which is incorporated herein by reference).

Essentially two treatment possibilities have proven themselves during recent decades for treatment of a destroyed hip joint head from which considerable pain sensations and serious functional restrictions of the joint result:

First, it is possible to provide the patient with an orthotic device, that is with an external support apparatus. In addition to the fact that this therapeutic possibility is completely unacceptable from a cosmetic point of view, it is also less than optimal from the perspective of therapeutic technology.

A further, more widely accepted possibility is to provide the patient with an endoprosthesis, namely a hip stem endoprosthesis, in which a stem is installed in the previously excavated bone marrow area of the femur and is there fixed with or without the use of cement. Such an endoprosthesis then offers the possibility of connection on its proximal side with an artificial spherical joint part.

It is precisely the latter possibility which is strongly represented in patent literature. At this point, reference is made only to DE-U-94 12 408 U1 as an example.

There are some approaches which are quite promising, with respect to long-term stability in the patient's body, among the various hip stem endoprostheses proposed in the patent literature. Sooner or later, however, for example after 10 to 15 years, subjection of the endoprosthesis to wear and tear is to be observed, which leads to the necessity of a revision intervention to remove the implanted endoprosthesis and replace it by a new one. This is certainly not wholly without problems, since a considerable portion of the natural bone material is removed in the initial implantation by the resection and clearing of the bone marrow area. The material once removed is then under the circumstances absent in a revision intervention. This then especially has the effect that, when the patients are relatively young, which one must assume from the beginning, they will be subjected to at least one revision intervention in the course of their lives.

An endoprosthesis which manages with a smaller resection of natural bone material than the known hip stem endoprostheses has become known from DE-A-27 24 234 C2. The prosthetic element described therein is implanted in the upper region of a femur, but below the lesser trochanter, without a stem extending into the bone marrow area. This prosthesis, which is also designated as a pressure plate prosthesis, basically reaches with a proximal pressure plate over the cortex of the resected femur in the area of the removed hip joint head. It is braced with a pressure plate, which lies laterally on the femur, in such a manner that all mechanical forces between the endoprosthesis and the femur are directly introduced into the cortical layer of the femur, whereby a mechanical strain on the spongiosa, which is felt to be impermissible, should be avoided. Only a small amount of bone cement is necessary for fixing the pressure plate in the proximal region.

As explained, underlying the philosophy of this prosthesis is the assumption that the spongiosa of the femur should be subjected to as little strain as possible. This is achieved at the expense of an extreme load upon the cortex of the femur, since namely all forces are loaded onto it and introduced into it. This in no way corresponds to natural conditions according to current knowledge.

Moreover, WO 89/11837 shows a prosthesis which operates quite similarly, in which the function of the proximal pressure according to the previously mentioned publication is undertaken by the specially constructed hip joint head, which is provided with an interior recess on which the resected femur stump is installed in the interior with creation of pressure.

Two prostheses, in which the main burden of the spongiosa of the femur bone is to be assumed, have become known from FR 26 26 169 A1 and FR 26 74 122 A1. In the first of the two named publications, there is provided a proximal threaded bolt, having a plug-in cone, for screwing into the spongiosa. This may lead to severe instability problems within a very short time. In the second of the two named publications a plate bearing a plug cone is fastened by means of a series of bone screws, wherein the bone screws reach into the spongiosa. Serious stability questions also arise from this, since the spongiosa by its nature can only be subjected to slight point load in comparison with the cortex of the femur bone.

SUMMARY OF THE INVENTION

Against this background, it is therefore an object of the present invention to provide a femur endoprosthesis for an artificial hip joint, which is considerably better adapted than the aforementioned prostheses to natural conditions with respect to the introduction of force into the femur, wherein resections of natural bone material become necessary only to a small extent.

This object is accomplished according to the present invention in that the femur endoprosthesis has (1) a stem which can be implanted without cement in the upper region of a femur below the greater trochanter, the proximal end of the stem being connectable with an adapter for accommodating an artificial spherical joint, wherein the exterior of the stem is at least partially covered with an open-meshed three-dimensional spatial lattice structure, and (2) a stem end bent caudally and constructed as a stem end, which is at least partially covered with an open-meshed three-dimensional spatial lattice structure.

In contrast to German patent 196 01 340, in accordance with the present invention no draw plate is provided which works together with a draw-in bolt, which penetrates the cortex of the femur bone. This penetration leads to a weakening of the femur bone.

In the present case, the bent end of the stem is instead that part which lies laterally on the cortical side of the natural spongiosa. The implant of the invention is thus to be anchored "flying free" in the spongiosa of the femur, whereas the implant according to German patent 196 01 340 has a fixed point or fulcrum in the form of a draw plate.

In the present case, the result is that the femur bone is in no way weakened from the outside. The construction is moreover simpler than that in accordance with German patent 196 01 340. The attachment of an artificial spherical joint takes place in the same way with a corresponding adapter.

Further advantageous refinements are described below and in the dependent claims.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings embodiment(s) which are presently preferred. It should be understood, however, that the invention is not limited to the precise arrangements and instrumentalities shown. In the drawings:

The single FIGURE is a schematic view of a femur endoprosthesis according to the invention shown implanted in a femur bone and with attached spherical hip joint part.

DETAILED DESCRIPTION OF THE INVENTION

Figure 1:
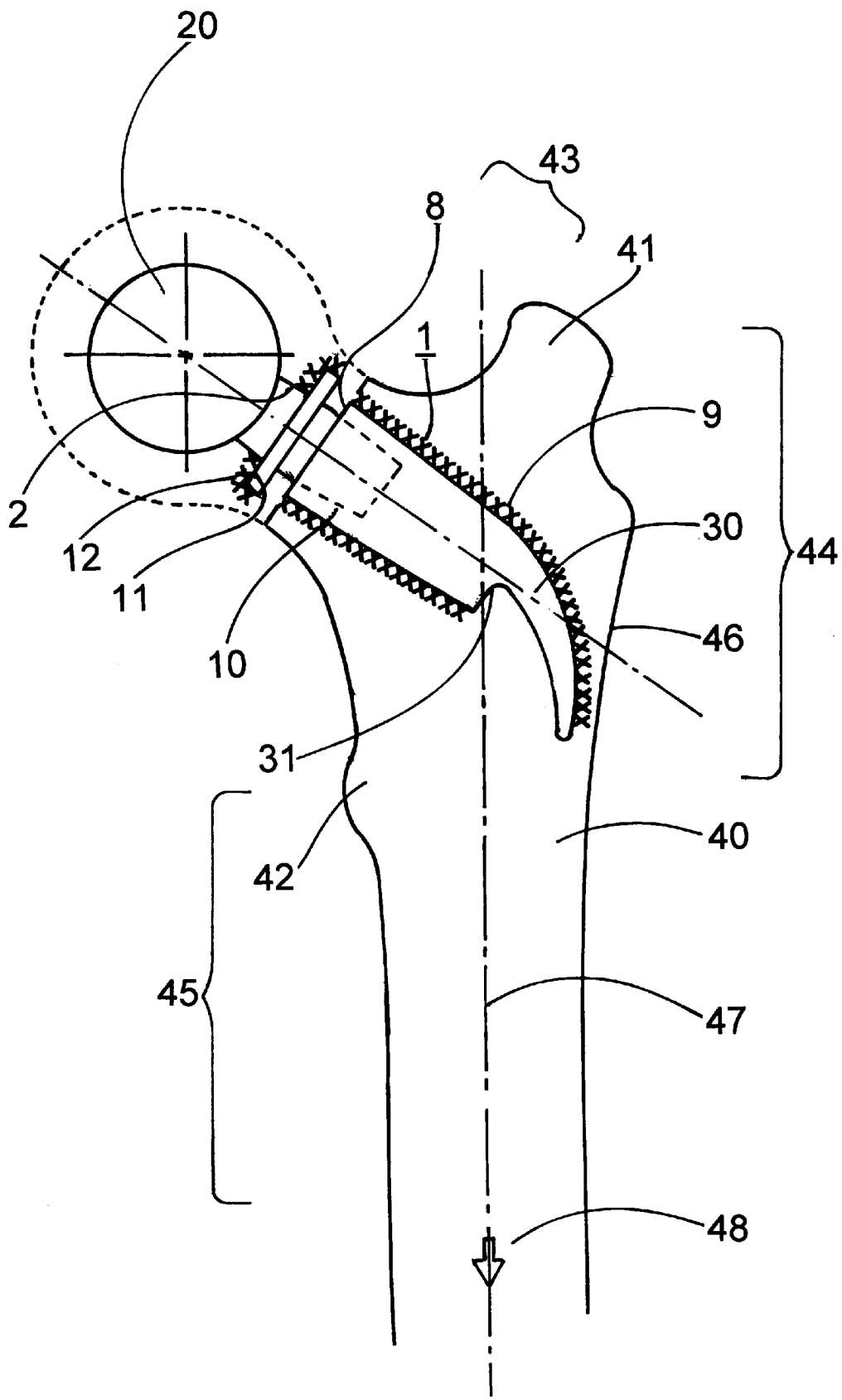

For purposes of illustrating an implantation position of a femur endoprosthesis according to the present invention in a femur, the parts of the femur bone are illustrated schematically in the sole FIGURE of drawings. In particular, the femur bone 40 has a greater trochanter 41 and a lesser trochanter 42 which essentially define the three major regions of the femur bone 40, namely the neck region 43 (above the greater trochanter 41), the metaphysial region 44 (between the greater and lesser trochanters 41, 42), and the diaphysial region 45 (below the lesser trochanter 42). For ease of reference, the cortex or outer surface of the femur is designated by 46, the longitudinal axis of the femur is designated by 47, and the caudal or downward direction is indicated by the arrow 48.

In the present invention, the stem 1 has a shape similar to the shell in accordance with German patent 196 01 340 with a conical taper from its proximal end 8 toward its distal end. In the distal area, however, the stem 1 transitions into a stem end 30 bent caudally, that is bent downwardly in the direction indicated by arrow 48, wherein the curvature is so proportioned that the outermost end of the stem end 30 comes to lie in a lateral area of the femur interior. As shown in the drawing, the step 31 in the transition area of the stem 1 into the stem end 30 intersects the longitudinal axis 47, and the stem end 30 lies laterally on the cortical side of the natural spongiosa (as stated above) and does not penetrate the cortex 46. As seen in the drawing, the neck region 43 above the greater trochanter is partially conserved.

The stem 1 is at least partially covered with an open-meshed three-dimensional lattice structure 9 just like the stem end 30. Open-meshed three dimensional lattice structures suitable for the endoprosthesis of the present invention are known in the art, for example from U.S. Pat. Nos. 5,178,201 and 5,433,750. Preferably, the lattice structure on stem exterior sides facing in caudal and cranial directions has a relatively coarse mesh, for example having mesh widths of about 2 to 6 mm, whereas the lattice structure on stem exterior sides facing in ventral and dorsal directions is preferably formed with a relatively fine mesh, for example having mesh widths of about 1 to 2.5 mm.

The attachment of an artificial spherical joint part 20 takes place with an adapter 2 constructed as a double plug cone, in the same manner as is provided in German patent 196 01 340. The double plug cone preferably has a peripheral flange 11 around a common base of the double cone, and the proximal end 8 of the stem 1 is provided with a conical sleeve 10 corresponding in shape to one end of the double plug cone for receiving and holding the adapter 2 with a pressure fit. Outward facing surfaces of the flange 11 may also be at least partially covered with an open meshed three-dimensional spatial lattice structure 12.

As is clearly recognizable, no part of the implant penetrates the cortex 46 of the femur bone 40, so that no weakening of the bone material takes place in this area. In cases where the femur endoprosthesis of the invention can be implanted, a more stable femur results.

It will be appreciated by those skilled in the art that changes could be made to the embodiment(s) described above without departing from the broad inventive concept thereof. It is understood, therefore, that this invention is not limited to the particular embodiment(s) disclosed, but it is intended to cover modifications within the spirit and scope of the present invention as defined by the appended claims.

What is claimed is:

1. A femur endoprosthesis for an artificial hip joint, comprising a stem (1) implantable without cement in a metaphysial region of a femur (40) below the greater trochanter while partially conserving the femoral neck, a proximal end (8) of the stem being connectable with an artificial spherical joint part (20), a distal end of the stem being bent caudally and constructed as a stem end (30), an exterior of the stem (1) and the stem end (30) being at least partially covered with a lattice structure, and the stem having a caudally oriented step (31) in an area of transition into the stem end (30).

2. The femur endoprosthesis according to claim 1, wherein the stem (1) is formed with a conical taper from its proximal end (8) up to a beginning of the bend of stem end (30).

3. The femur endoprosthesis according to claim 1, wherein the lattice structure is an open-meshed three-dimensional spatial lattice structure (9).

4. The femur endoprosthesis according to claim 3, wherein the spatial lattice structure (9) is formed on stem exterior sides facing in caudal and cranial directions with a coarse mesh having mesh widths of about 2 to 6 mm.

5. The femur endoprosthesis according to claim 3, wherein the spatial lattice structure (9) is formed on stem exterior sides facing in ventral and dorsal directions with a fine mesh having mesh widths of about 1 to 2.5 mm.

6. The femur endoprosthesis according to claim 1, wherein the proximal end (8) is connectable to the artificial spherical joint part (20) by an adapter (2).

7. The femur endoprosthesis according to claim 6, wherein the adapter (2) is constructed substantially as a double plug cone having a peripheral flange (11) around a common base of the double cone, wherein a conical sleeve (10) corresponding in shape to one end of the double plug cone is provided in a proximal area of the stem (1).

8. The femur endoprosthesis according to claim 1, wherein outward-facing surfaces of the flange (11) are at least partially covered with an open-meshed three-dimensional spatial lattice structure (12).

9. The femur endoprosthesis according to claim 1, wherein the step (31) intersects a longitudinal axis (47) of the femur when implanted into the metaphysial region.

10. A method of implanting a femur endoprosthesis for an artificial hip joint, comprising the steps of:

providing a stem (1) adapted for implantation without cement in a metaphysial region of a femur (40) and below the greater trochanter in natural spongiosa, the stem having a stem end (30) with a distal portion which is bent caudally, an exterior of the stem (1) and the stem end (30) being at least partially covered with a lattice structure, and a caudally oriented step (31) in an area of transition into the stem end (30);

implanting the stem with only a proximal end (8) of the stem (1) protruding from the femur;

positioning the stem (1) so that the caudally bent distal portion of the stem end (30) is generally parallel to a longitudinal axis (47) of the femur and lies laterally on a cortical side of the natural spongiosa; and connecting the proximal end (8) with an artificial spherical joint part (20).

11. The method according to claim 10, wherein the proximal end (8) is connected to the artificial spherical joint part (20) by an adapter (2).

12. The method according to claim 10, wherein the lattice structure is an open-meshed three-dimensional spatial lattice structure (9).

* * * * *